(12) United States Patent
Bruder et al.

(10) Patent No.: US 7,656,992 B2
(45) Date of Patent: Feb. 2, 2010

(54) METHOD FOR DETERMINING MOVEMENT AND REST PHASES OF A PARTIAL OBJECT THAT MOVES AT TIMES DURING A CT EXAMINATION, AND CT SYSTEM

(75) Inventors: Herbert Bruder, Höchstadt (DE); Thomas Flohr, Uehlfeld (DE)

(73) Assignee: Siemens Aktiengesellschaft, Munich (DE)

( * ) Notice: Subject to any disclaimer, the term of this patent is extended or adjusted under 35 U.S.C. 154(b) by 91 days.

(21) Appl. No.: 11/978,580

(22) Filed: Oct. 30, 2007

(65) Prior Publication Data

US 2008/0130829 A1 Jun. 5, 2008

(30) Foreign Application Priority Data

Oct. 31, 2006 (DE) .................. 10 2006 051 475

(51) Int. Cl.
*A61B 6/03* (2006.01)
(52) U.S. Cl. .............................. 378/8; 378/9
(58) Field of Classification Search ............ 378/8, 378/9, 98.5
See application file for complete search history.

(56) References Cited

U.S. PATENT DOCUMENTS

| | | | | |
|---|---|---|---|---|
| 4,991,190 A | * | 2/1991 | Mori ........................ | 378/9 |
| 6,381,487 B1 | | 4/2002 | Flohr et al. | |
| 6,421,412 B1 | * | 7/2002 | Hsieh et al. ................ | 378/9 |
| 6,650,726 B2 | | 11/2003 | Sembritzki et al. | |
| 6,760,399 B2 | * | 7/2004 | Malamud .................. | 378/9 |
| 2005/0089134 A1 | * | 4/2005 | Bruder et al. ............. | 378/9 |
| 2005/0190878 A1 | * | 9/2005 | De Man et al. ........... | 378/9 |
| 2006/0193430 A1 | * | 8/2006 | Kuhn ........................ | 378/9 |

FOREIGN PATENT DOCUMENTS

| | | |
|---|---|---|
| DE | 198 54 939 | 11/2001 |
| DE | 101 23 797 | 12/2002 |
| DE | 103 02 565 | 8/2004 |

OTHER PUBLICATIONS

Chalmer et al., Understanding statistics, Published by CRC Press, (1986), p. 214.*

* cited by examiner

*Primary Examiner*—Chih-Cheng G Kao
(74) *Attorney, Agent, or Firm*—Harness, Dickey & Pierce, P.L.C.

(57) ABSTRACT

A method and a CT system are disclosed for determining movement and rest phases of a partial object that moves at times in an examination object during a CT examination. In at least one embodiment, at least two different radiation sources are used for the comparative measurement, and a first radiation source emits a first fan beam at a specific rotation angle at a first instant, the absorption of said beam being measured in beamwise fashion, a second radiation source emits a second fan beam, at the same rotation angle at a second, later instant, the absorption of the beam likewise being measured in beamwise fashion, and the relative movement or relative rest of the partial object between the first and second instants is deduced by comparing deviating absorption values of a multiplicity of spatially equivalent and equidirectional fan beams proceeding from the same angular position of the radiation sources.

25 Claims, 3 Drawing Sheets

METHOD FOR DETERMINING MOVEMENT AND REST PHASES OF A PARTIAL OBJECT THAT MOVES AT TIMES DURING A CT EXAMINATION, AND CT SYSTEM

PRIORITY STATEMENT

The present application hereby claims priority under 35 U.S.C. §119 on German patent application number DE 10 2006 051 475.0 filed Oct. 31, 2006, the entire contents of which is hereby incorporated herein by reference.

FIELD

Embodiments of the invention generally relate to a method for determining movement and rest phases of a partial object that moves at times in an examination object. For example, the partial object may be that of a beating heart or of a moving thorax in a patient. The method, in at least one embodiment, may be carried out during a CT examination for example, wherein the examination object is scanned by at least one radiation source that rotates around the examination object, and at least one detector is used in measuring and comparing the absorption of the scanning radiation upon passage through the examination object on the same radiation path at successive instants.

Embodiments of the invention furthermore generally relate to a CT system for carrying out such a method, such as one comprising at least two radiation sources arranged in angularly offset fashion around the system axis, for example.

BACKGROUND

A method is known for example from the patent specification DE 198 54 939 C2. In accordance with the patent specification, the rest phase of a beating heart is established here by an automatic analysis of the measurement data of a single-source CT apparatus and comparison of the complementary projections in parallel geometry. In this case, complementary projections are understood to mean projections offset by an angle of 180°, such that each beam of these projections has a complementary partner having the same path but in the opposite direction.

In the case of unmoving objects, it can be assumed to a first approximation that the difference between the complementary beams of the complementary projections is equal to 0 apart from negligible noise contributions. In the case of moving objects or partly moving objects, the deviation of the difference from 0 which goes beyond the noise contribution is a measure of the movement of the measured object during half a revolution time of the CT scanner. In this case, the sum of the absolute deviations of the complementary parallel projections can be regarded as a suitable coefficient of measure $\sigma_n$.

This measure of movement $\sigma_n$ can be plotted as a function of the projection angles and thus as a function of time. If the measure of movement $\sigma_n$ lies below a specific threshold value, then it is assumed that the heart was in the rest phase in the time between the measurement of the two complementary projections.

This method has some disadvantages. Firstly, the time difference between the complementary projections corresponds to half a rotation time, that is to say according to the current prior art not less than 0.33 s/2=165 ms. That is relatively long compared with typical time constants of heart movement. Under certain circumstances, therefore, all movements which take place within this time window of 165 ms cannot be registered or can be registered incorrectly.

Secondly, the method is based on the analysis of parallel projections. Present-day CT apparatuses record fan projections, however, from which the parallel projections first have to be generated by interpolation. A parallel projection is then composed of measured values of fan projections measured at different instances, such that the assignment of a specific recording time to a parallel projection is difficult and can relate approximately only to the rotation center.

SUMMARY

In at least one embodiment the invention, a method is disclosed for determining movement and rest phases of a partial object that moves at times in an examination object. In at least one embodiment, the method may permit an improved time resolution and/or an improved unambiguity of the measured values with regard to their instant in time.

The inventors have recognized that it is advantageous, in the case of at least one embodiment of a CT system having at least two radiation sources arranged in angularly offset fashion around the system axis, to compare fan projections instead of parallel projections recorded in a manner smeared over time, the fan projections being recorded at the same angular position—not of the gantry but of the radiation sources—by way of the two radiation sources at different times. This has the advantage, on the one hand, that the recording instant of a projection is defined very unambiguously and is not greatly smeared over time. Moreover, it is also particularly advantageous in this case that the beam direction is identical in the projections recorded in temporally offset fashion, such that possible hardening artifacts which, under certain circumstances, could also lead to different absorption results are avoided.

If, in a dual-source CT, for example, the same z-position of the moving object is successively scanned by the two measuring systems at a time interval of a quarter of a revolution, then a time interval for two projections of this type of 0.33 s/4=83 ms results, according to the rotational speeds calculated in the current prior art. In this case, too, the absolute difference between the individual beams can be used as a measure of the partial movement of the object or else the complete movement of the object and such a movement can be assumed as soon as a threshold corresponding to the sum of the noise contributions is exceeded.

Instead of half a revolution time of the CT scanner, now a quarter of a revolution time of a CT scanner becomes necessary in order to enable difference formation, such that the time resolution is halved in comparison with the method using parallel projections. The heart movement with its typical time constants can thus be scanned significantly better with respect to time. Moreover, the method can thus also be applied to the detection of other rapid temporal processes, such as the inflow of contrast medium. Furthermore, it is now no longer necessary to perform a reinterpolation of measurement data before the determination of absorption differences, rather it is possible to utilize the directly measured fan projection. Consequently, the problem of the time indeterminacy of the individual parallel projections is also obviated.

In accordance with the above-described basic concept of at least one embodiment of the invention, the inventors propose improving the known method for determining movement and rest phases of a partial object that moves at times in an examination object, preferably of a beating heart or of a moving thorax in a patient, during a CT examination, wherein, as is known, the examination object is scanned by at least one radiation source that rotates around the examination object, and at least one detector is used in measuring and comparing the absorption of the scanning radiation upon passage through the examination object on the same radiation path at successive instants.

An improvement of the method according to at least one embodiment of the invention resides in the fact that at least two different radiation sources are used for the comparative measurement, wherein a first radiation source emits a first fan beam at a specific rotation angle at a first instant, the absorption of said beam being measured in beamwise fashion, a second radiation source emits a second fan beam, at the same rotation angle at a second, later instant, the absorption of said beam likewise being measured in beamwise fashion, and the relative movement or relative rest of the partial object between the first and second instants is deduced by comparing deviating absorption values of a multiplicity of spatially equivalent and equidirectional fan beams proceeding from the same angular position of the radiation sources.

Thus, two, three or more radiation sources are used, which, at different instants, are situated at the same angular position with respect to the system axis, and the change in the absorption in the fan beam emitted there is measured on an opposite detector. If no changes or only changes in the range of statistical noise are present, then a rest phase or motionlessness of the examination object or of parts of the examination object can be assumed, while a movement of the examination object or of parts of the examination object can be assumed as soon as changes with respect to the absorption values result which lie above a difference sum arising from the sum of individual noise artifacts of the measured beams.

An advantage of this measuring method of at least one embodiment over the method of comparing parallel projections that is known in the prior art is that the instant of the measurement of all the beams of a projection is clearly defined and is not smeared over a relatively large angular range of the focus along its circular path around the z-axis in order to collect parallel beams. Moreover, it is also in this case not just necessary to make interpolation calculations, rather it is possible to directly evaluate detector data representing the sum of the fan beams which are considered.

Furthermore, it is advantageous in at least one embodiment of this method that beams having the same propagation direction are now compared with one another, such that possibly different hardening effects, depending on the direction of the radiation course, are no longer of significance.

In at least one embodiment, the inventors furthermore propose carrying out this differential measurement or comparative measurement not just at one specific angular position, but rather at progressive angular positions of the radiation sources. In this way, a complete time profile of the movement of a partial object or of the movement of the examination object can be recorded and, if appropriate, periodic time sequences of rest phases and movement phases can also be recorded, and their result can be utilized for the selection of measurement data for the later reconstruction. Such selection methods, or the use of measurement data from predetermined movement phases or rest phases of a periodically moving object, in particular of a heart, are generally known and can be combined with the methods described here.

At least one embodiment of the method described can be performed either with at least two fan beams having identical fan angles or else with at least two radiation sources which emit fan beams having different fan angles, wherein, in the latter case, exclusively overlapping ranges of the fan angles should be used for the comparison. There is supplementarily the possibility of also using only partial sections, preferably a central segment of beams of the radiation fans, for the comparative measurements. As an alternative, it is also possible to use only a coarse grid of beams of the radiation fans, that is to say a subset of the beams, for the comparative measurements.

At least one embodiment of the above-described method can preferably be used in a CT system with two radiation sources offset by 90°, in which case the time resolution of the measuring method is improved by a factor of two in comparison with the complementary parallel projections. As an alternative, there is also the possibility of using a CT system with three radiation sources offset by 120°, wherein here the time resolution is worsened by a third in comparison with a system with two radiation sources offset by 90°.

It is pointed out that the abovementioned variants of the CT systems in which at least one embodiment of the method is preferably utilized only represent favorable example variants, other angular offsets of radiation sources expressly not being ruled out.

Preferably, at least one embodiment of the method mentioned can be utilized in conjunction with radiation sources that move on a circular path relative to the examination object. This variant has the advantage that at identical angular positions of the radiation sources, the focus is also actually at the identical location in the z-direction, such that the radiation fans emitted—given an identical fan size—are congruent. However, there is also the possibility of using at least one embodiment of the method described in conjunction with radiation sources that are moved on a spiral path relative to the examination object, particularly if relatively small advances are involved here, as is the case in cardio-examination methods. In this case, the small offset of the radiation sources in the z-direction is largely ignored, it being favorable in this case for the threshold value starting from which the movement of the examination object is defined to be raised somewhat in order that small changes are not detected as movement artifacts.

One possibility for compensating for the effect of such an offset in the z-direction at least to an extent consists in the fact that when a multirow detector is used, only beams which originate from detector elements without a relative z-offset with respect to one another are taken into account in the comparative measurements. That is to say that for example when using a multirow detector and a z-offset corresponding in the case of radiation sources offset by 90°, to the distance between two detector rows in a quarter of a revolution, therefore, in the case of the first measurement rows 1 to n−1 are compared with the measurement data of rows 2 to n in the case of the second measurement. The effect of the z-offset can be at least partially reduced by this.

Another possibility of at least one embodiment resides in using a CT system which is equipped with at least two radiation sources which are offset in the z-direction and which rotate on an identical spiral path during operation. This has the effect that the foci of the radiation sources, given identical rotation angles, are also positioned at the same z position.

Correspondingly, there is also the possibility of arranging the detectors of the CT system offset in the z direction, such that they also rotate along a single identical spiral path in the spiral operating mode.

The inventors furthermore propose that, in at least one embodiment, the sum of the absolute deviations of the fan beams under consideration or the sum of the squares of the deviations of the fan beams under consideration are preferably utilized as a measure of the presence of movement.

Moreover, in at least one embodiment, the inventors also propose improving a CT system for generating tomographic representations of an examination object containing a partial object that moves at times, preferably of a patient with a beating heart or a moving thorax, wherein this system is equipped with at least two radiation sources which are arranged in an angularly offset manner and which rotate about a system axis and transirradiate the examination object, while the absorption of the radiation is measured, and a control and computation unit with a memory containing program code which, during operation, evaluates the recorded measurement data and reconstructs the tomographic representations. At least one embodiment of the invention here intends program code which carries out the method steps of the above-described method to be present in the memory of the control and computation unit.

BRIEF DESCRIPTION OF THE DRAWINGS

Embodiments of the invention are described in more detail below with reference to the figures, wherein only the features required for understanding the invention are illustrated. The following reference symbols are used in this case: 1: CT system; 2: first x-ray tube; 3: first detector housing; 4: second x-ray tube; 5: second detector housing; 6: gantry housing; 7: patient; 8: patient's couch; 9: system axis/z axis; 10: control and computation unit; 11: memory; 12: path of the focus for the first parallel projection; 13: path of the focus for the complementary parallel projection with respect to the first parallel projection; 14: heart; 14': heart in the contracted state; $D_1$: first detector; $D_2$: second detector; $D_3$: third detector; $F_1$: first focus; $F_2$: second focus; $F_3$: third focus; $P_{\alpha,i}$: projection beams; $P_{\alpha+180°,i}$: projection beams; $Prg_i$: i-th program; $S_{j,i}$: i-th beam of the j-th radiation fan; $\alpha_i$: rotation angle; $\beta_1$, $\beta_2$: fan angle.

Specifically in the figures.

DETAILED DESCRIPTION OF THE EXAMPLE EMBODIMENTS

Figure 1:
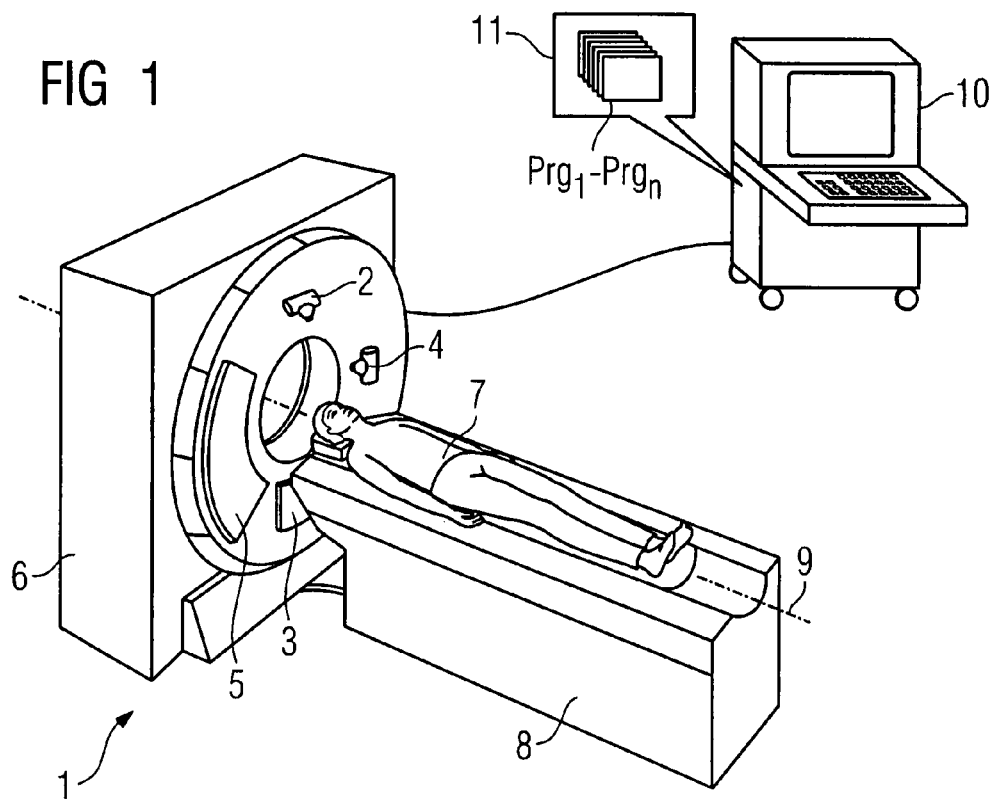
FIG. 1 shows a schematic 3D illustration of a CT system according to an embodiment of the invention.

The terminology used herein is for the purpose of describing particular embodiments only and is not intended to be limiting of the present invention. As used herein, the singular forms "a", "an", and "the" are intended to include the plural forms as well, unless the context clearly indicates otherwise. It will be further understood that the terms "includes" and/or "including", when used in this specification, specify the presence of stated features, integers, steps, operations, elements, and/or components, but do not preclude the presence or addition of one or more other features, integers, steps, operations, elements, components, and/or groups thereof.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

In describing example embodiments illustrated in the drawings, specific terminology is employed for the sake of clarity. However, the disclosure of this patent specification is not intended to be limited to the specific terminology so selected and it is to be understood that each specific element includes all technical equivalents that operate in a similar manner.

Referencing the drawings, wherein like reference numerals designate identical or corresponding parts throughout the several views, example embodiments of the present patent application are hereafter described. Like numbers refer to like elements throughout. As used herein, the terms "and/or" and "at least one of" include any and all combinations of one or more of the associated listed items.

FIG. 1 shows a CT system 1 according to an embodiment of the invention with two tube-detector systems arranged offset by 90°. In a gantry housing 6, a first x-ray tube 2 with a detector housing 3 lying opposite are arranged on a gantry and a second x-ray tube 4 with a detector housing 5 likewise lying opposite is arranged offset by an angle of 90° about a system axis 9 on said gantry. A patient 7 is situated on a movable patient's couch 8, which can be shifted along the system axis 9 through the scanning region of the two tube-detector systems. This system is controlled by a control and computation unit 10 having in a memory 11, program code in the form of programs $Prg_1$ to $Prg_n$, which, during operation, perform both the control of the CT system and the evaluation of the measurement data and reconstruction of the tomographic recordings.

According to an embodiment of the invention, the control and computation unit 10 or the memory 11 thereof, also contains program code which, through a comparison of the detector output data of the two tube-detector systems at the same rotation angle about the system axis 9, determines whether the patient's heart, for example, is in a rest or movement phase. The distinction is made by virtue of the fact that the detector data measured at two different instants in the same angular position are compared with one another and the absolute deviations in the fan projections are determined, a rest phase being assumed if the deviation falls below a threshold value corresponding approximately to the sum of the noise over the detector elements under consideration, while movement of the heart is indicated when said threshold value is exceeded, a certain safety margin being added to said threshold value, if appropriate.

The method according to an embodiment of the invention which is used in this case will be described again in more detail in the subsequent figures.

Figure 2:
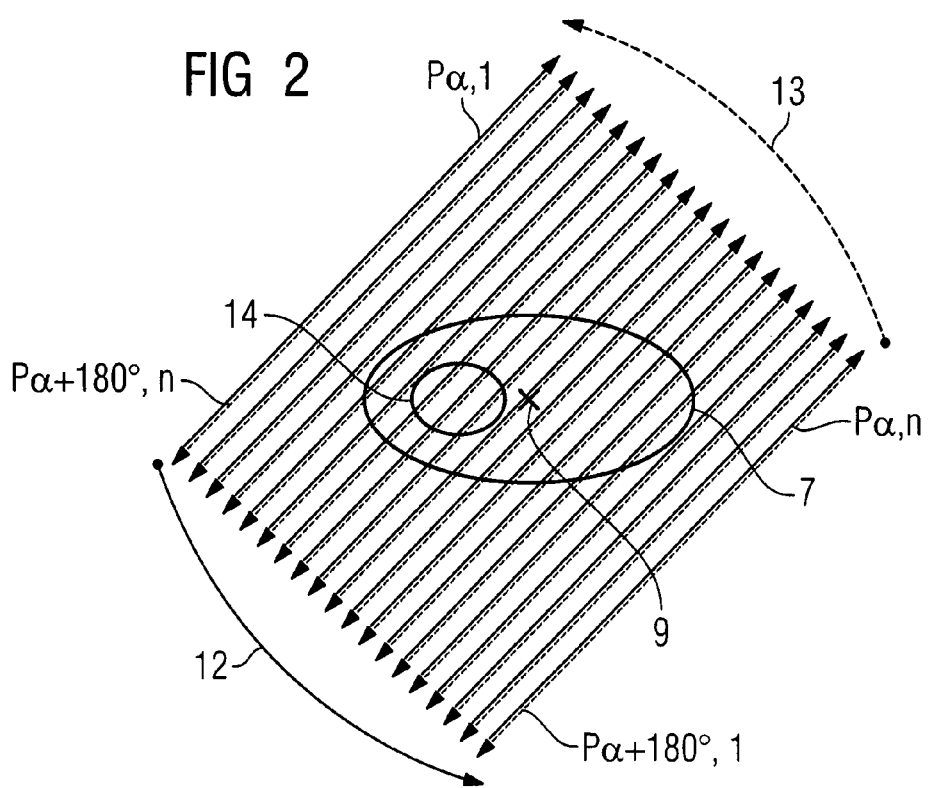
FIG. 2 shows a schematic illustration of the method of comparing parallel projections that is known in the prior art.

FIG. 2 shows, for the purpose of understanding, first of all the method with parallel projections that is known from the prior art. In this case, during the revolution of a focus, the absorption values of a fan beam emerging from the focus F or F' are measured at a multiplicity of rotation angles for a multiplicity of individual beams. In order to determine parallel projections, all of the beams $P_{\alpha,1}$-$P_{\alpha,n}$ having a specific projection angle are collected or, if these are not present, are determined by interpolation. In order to obtain all the beams $P_{\alpha,1}$-$P_{\alpha,n}$ the focus F must cover the path 12 designated by 12 in FIG. 2, which requires a certain period of time. Consequently, all the beams $P_{\alpha,1}$-$P_{\alpha,n}$ have a different datum with respect to which they were determined.

The same then happens on the opposite side offset by 180° when the focus F' covers the path 13 and the parallel projection beams $P_{\alpha+180°,1}$-$P_{\alpha+180°,n}$ are detected with regard to their absorption values in the process. If a patient 7 whose heart 14 is in a rest phase is then situated in the region of the radiation, no significant difference results from the differences between the oppositely running projections, while differential values that are significantly increased arise in the case of a moving heart 14. Rest and movement phases can now be distinguished by virtue of this increase in the differential values.

What is problematic in this case is that firstly each individual parallel projection does not have a clear datum but rather a time range and, moreover, the period of time between the two measurements of the complementary projections is relatively long since the radiation source has to cover a path of more than 180° for this purpose.

Figure 3:
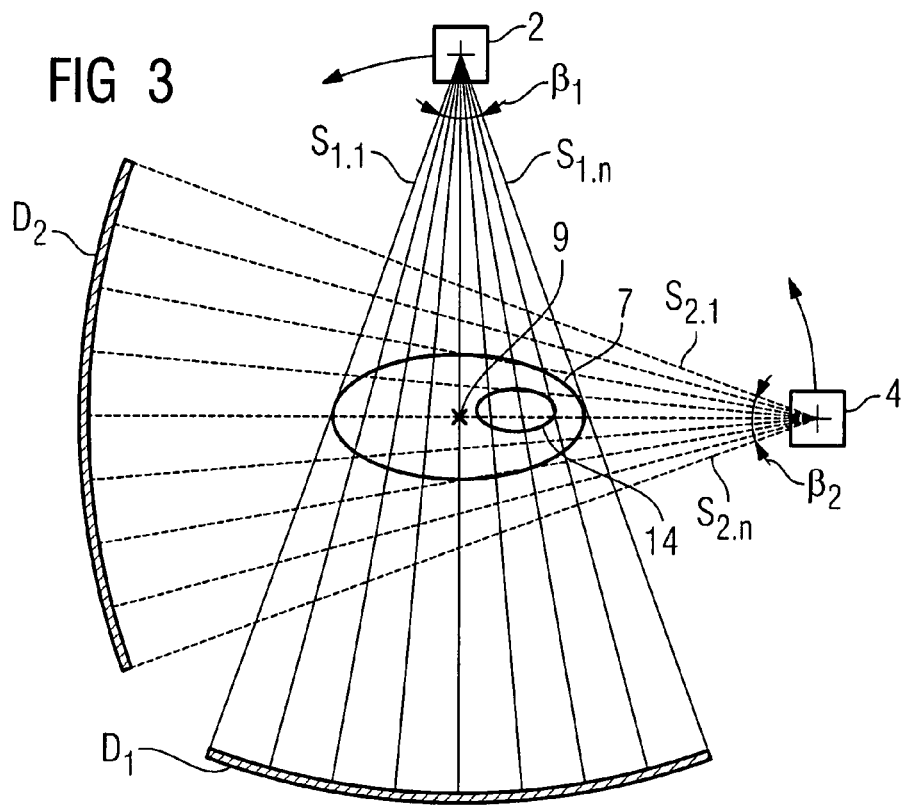
FIG. 3 shows a schematic illustration of a CT system with two radiation sources offset by 90°.
Figure 4:
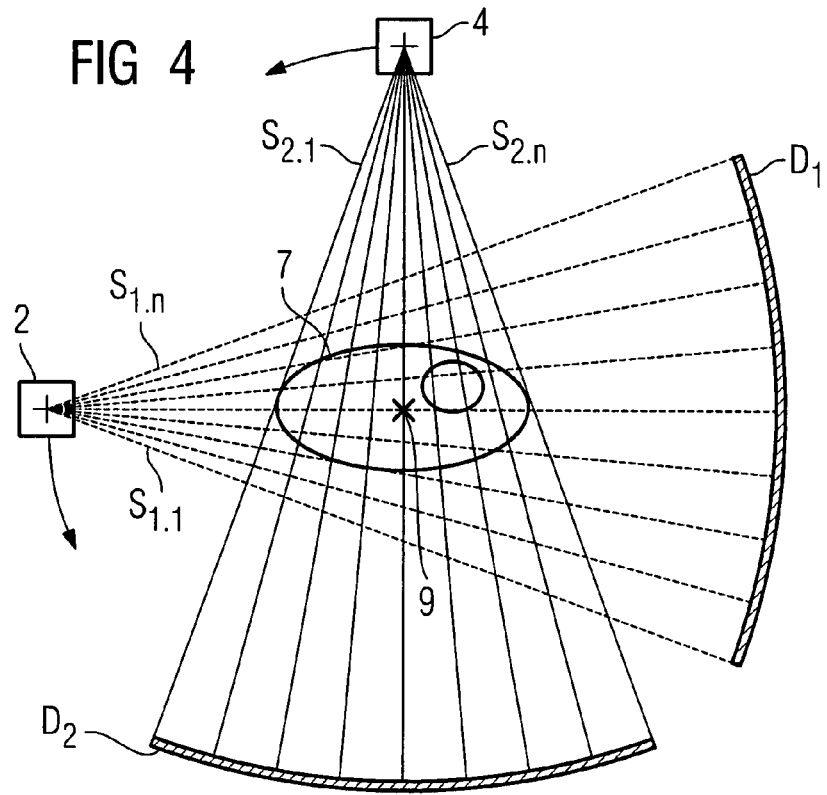
FIG. 4 shows a CT system from FIG. 3 after a 90° rotation of the radiation sources.

An embodiment of the invention proposes using fan projections instead of parallel projections, wherein the measurements of the fan projections are not permitted to be performed in a manner offset by 180°, but rather should in each case be performed at the same angular position. FIGS. 3 and 4 by way of example show such a measurement with a CT system 1 with two x-ray tubes offset by 90°.

A first x-ray tube 2 and a second x-ray tube 4 can be discerned in cross section in FIG. 3. A first detector 3 and a second detector 5 are respectively arranged opposite them. The two x-ray tubes and the two detectors are fixed on a gantry (not illustrated here) and rotate about a system axis around a patient 7, in whom a heart 14 is illustrated schematically. A beam fan comprising the beams $S_{1,1}$ to $S_{1,n}$ emerges from the x-ray tube 2, while a second beam fan $S_{2,1}$ to $S_{2,n}$ extends from the x-ray tube 4 to the detector 5 lying opposite.

The two FIGS. 3 and 4 differ to the effect that in FIG. 4 the two tube-detector systems have moved counterclockwise by an angle of 90° about the system axis. Accordingly, in FIG. 4, the second tube-detector system 4, 5 has attained the angular position which the first tube-detector system 2, 3 had in FIG. 3. Accordingly, it is now possible to compare the measurement results from the first beam fan $S_{1,1}$ to $S_{1,n}$ with the measurement results of the second beam fan $S_{2,1}$ to $S_{2,n}$ precisely at the instants at which the two x-ray tubes reached their twelve o'clock position. If there is a moving object, for example a beating heart, in the patient 7, then it is possible to ascertain by means of the difference, that is to say by forming the difference between the individual beams, whether the heart 14 changed, that is to say moved, between the instant from FIG. 3 and the instant of the recording in FIG. 4.

An advantage of an embodiment of this method compared with the method using parallel projections described in FIG. 2 is that 1. the instants at which the individual projections are recorded are unambiguously defined,
2. the time interval of the comparison between the two projections has become significantly shorter and
3. possible artifacts due to different beam hardening of the individual beams when passing through the patient in different directions, in particular for example when metallic prostheses or the like are present, can no longer occur, such that no false positive movement detections can take place as a result.

It is thus possible, therefore, to ascertain the beginning of the movement significantly more exactly and, with regard to the selection of the measurement data to be used, for the reconstruction, to be able to find greater certainty with regard to the data associated with the rest phase.

In principle, an embodiment of the method described above is possible both with focus-detector systems moved purely circularly around the patient and with spiral scanning since, in the case of spiral scanning, the advance values between two measurement points are relatively small and resultant differences in absorption can thus be disregarded.

Figure 5:
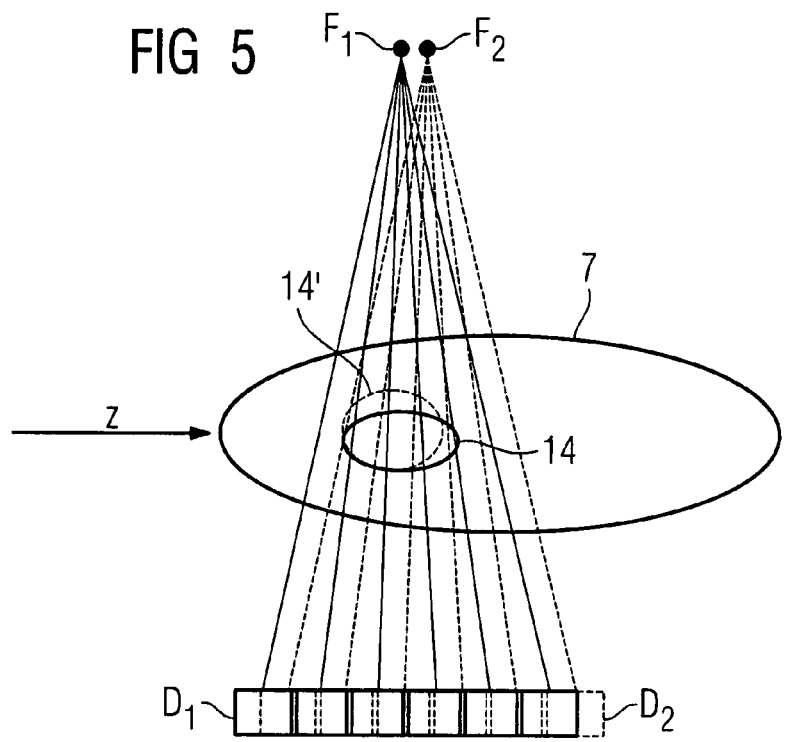
FIG. 5 shows a schematic illustration of a CT system in longitudinal section along the system axis with a simultaneous illustration of two foci at the same rotation angle.

FIG. 5 illustrates such a situation. This figure shows a first focus $F_1$ with a beam bundle emerging from the latter onto a multirow detector $D_1$, which scans a patient 7, and using dashed lines a later instant at which the focus $F_2$ of the second tube-detector system is in the same angular position, both the focus $F_2$ and the detector $D_2$ shown having a small offset in the z direction. This problem can at least partly be solved by arranging either the detectors or the foci or both on the gantry in such a way that they move in accordance with the advance on a single spiral path, such that focus and/or detector are situated at identical angular positions also in identical z-positions.

Figure 6:
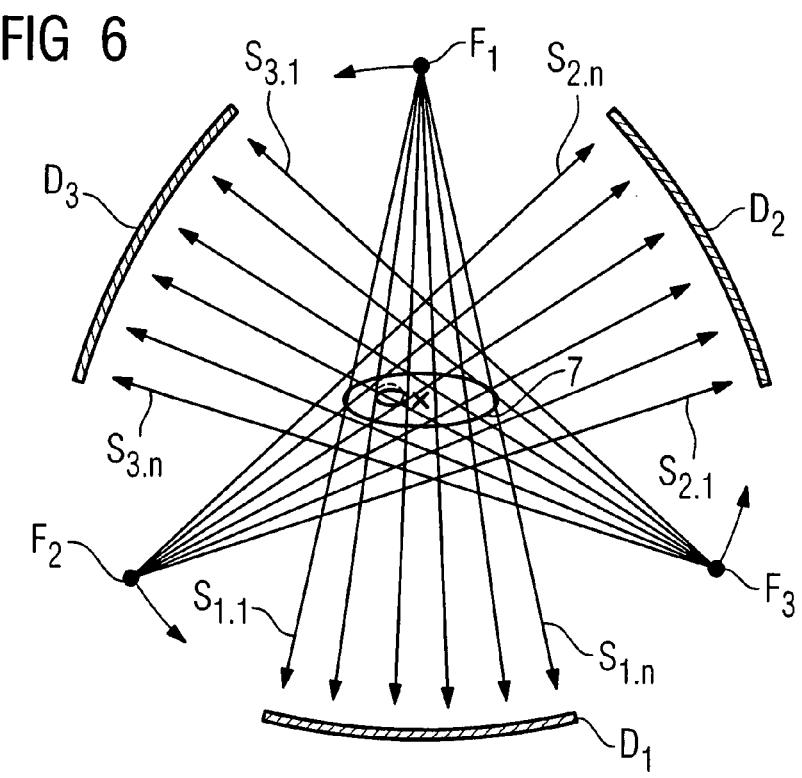
FIG. 6 shows a schematic illustration of a CT system with three radiation sources arranged offset by 120°, in cross section.

FIG. 6 supplementarily illustrates yet another variant of a CT system with three focus-detector systems, wherein the focus-detector systems $F_i$, $D_i$ with the radiation fans $S_{i,1}$ to $S_{i,n}$ are arranged offset by 120° in each case around the system axis. Such an arrangement of focus-detector systems likewise enables a movement detection in accordance with an embodiment of the method outlined above, although the time resolution turns out to be somewhat less favorable in comparison with a double focus-detector system.

It goes without saying that the abovementioned features of the invention can be used not only in the combination respectively specified, but also in other combinations or by themselves, without departing from the scope of the invention.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program and computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a computer readable media and is adapted to perform any one of the aforementioned methods when run on a computer device (a device including a processor). Thus, the storage medium or computer readable medium, is adapted to store information and is adapted to interact with a data processing facility or computer device to perform the method of any of the above mentioned embodiments.

The storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for determining movement and rest phases of a partial object that moves at times in an examination object, the method comprising:
    scanning the examination object using at least a first and a second x-ray radiation source that rotate around the examination object;
    using at least one detector in measuring and comparing absorption of the scanning radiation upon passage through the examination object on a same radiation path at successive instants, the at least first and second x-ray radiation sources being used for the comparative measurement, wherein
        the first x-ray radiation source emitting a first fan beam at a specific rotation angle at a first instant, the absorption of the fan beam being measured in beamwise fashion,
        the second x-ray radiation source emitting a second fan beam, at the same rotation angle at a second, relatively later instant, the absorption of the second fan beam likewise being measured in beamwise fashion, and wherein
            at least one of relative movement and relative rest of the partial object, between the first and second instants, is deduced by comparing deviating absorption values of a multiplicity of spatially equivalent and equidirectional fan beams proceeding from a same angular position of the x-ray radiation sources.

2. The method as claimed in claim 1, wherein a multiplicity of comparative measurements take place at progressive angular positions of the x-ray radiation sources.

3. The method as claimed in claim 2, wherein at least two x-ray radiation sources have fan beams having identical fan angles.

4. The method as claimed in claim 1, wherein at least two x-ray radiation sources have fan beams having identical fan angles.

5. The method as claimed in claim 1, wherein at least two x-ray radiation sources have fan beams having different fan angles, and wherein exclusively overlapping ranges of the fan angles are used for the comparison.

6. The method as claimed in claim 1, wherein only a central segment of beams of radiation fans is used for the comparative measurements.

7. The method as claimed in claim 1, wherein only a coarse grid of beams of radiation fans is used for the comparative measurements.

8. The method as claimed in claim 1, wherein a CT system having two x-ray radiation sources offset at 90° is used.

9. The method as claimed in claim 1, wherein a CT system having three x-ray radiation sources offset by 120° is used.

10. The method as claimed in claim 1, wherein the x-ray radiation sources are moved on a circular path relative to the examination object.

11. The method as claimed in claim 1, wherein the x-ray radiation sources are moved on a spiral path relative to the examination object.

12. The method as claimed in claim 11, wherein a pitch of the spiral path and a z-offset are disregarded in the comparative measurements.

13. The method as claimed in claim 11, wherein the at least one detector includes at least one multirow detector and only beams which originate from detector elements without a relative z-offset with respect to one another are taken into account in the comparative measurements.

14. The method as claimed in claim 11, wherein a CT system having at least two x-ray radiation sources which are offset in a z-direction and which rotate on an identical spiral path during operation is used.

15. The method as claimed in claim 14, wherein detectors of the CT system are also arranged offset in the z-direction and rotate on a single identical spiral path in a spiral operation mode.

16. The method as claimed in claim 1, wherein the sum of the absolute deviations of the fan beams under consideration is used as a measure of a presence of movement.

17. The method as claimed in claim 1, wherein a sum of the squares of the deviations of the fan beams under consideration is used as a measure of a presence of movement.

18. The method as claimed in claim 1, wherein the partial object, that moves at times in an examination object, is at least one of a beating heart and a moving thorax in a patient.

19. A computer readable medium Including program segments for, when executed on a computer device, causing the computer device to implement the method of claim 1.

20. A CT system for generating tomographic representations of an examination object containing a partial object that moves at times, comprising:
    at least two x-ray radiation sources, arranged in an angularly offset manner and which rotate about a system axis and transirradiate the examination object, absorption of the x-ray radiation being measurable;
    a control and computation unit, including a memory containing program code which, during operation of the control and computation unit, is configured to evaluate measured and recorded absorption measurement data and to reconstruct tomographic representations, the program code being configured to carry out,
        scanning the examination object using a first x-ray radiation source to rotate around the examination object and to emit a first fan beam at a specific rotation angle at a first instant, and a second x-ray radiation source to rotate around the examination object and to emit a second fan beam, at the same rotation angle at a second, relatively later instant,
        measuring absorption of the scanning radiation upon passage through the examination object on a same radiation path at successive instants, and comparing deviating absorption values of a multiplicity of spatially equivalent and equidirectional fan beams proceeding from the same angular position of the x-ray radiation sources to deduce at least one of relative movement and relative rest of the partial object, between the first and second instants.

21. A method for determining movement and rest phases of a partial object that moves at times in an examination object, the method comprising:
   scanning the examination object using a first x-ray radiation source to rotate around the examination object and to emit a first fan beam at a specific rotation angle at a first instant, and a second x-ray radiation source to rotate around the examination object and to emit a second fan beam, at the same rotation angle at a second, relatively later instant;
   measuring absorption of the scanning radiation upon passage through the examination object on a same radiation path at successive instants; and
   comparing deviating absorption values of a multiplicity of spatially equivalent and equidirectional fan beams proceeding from the same angular position of the x-ray radiation sources to deduce at least one of relative movement and relative rest of the partial object, between the first and second instants.

22. The method as claimed in claim 21, wherein a multiplicity of comparative measurements take place at progressive angular positions of the x-ray radiation sources.

23. The method as claimed in claim 21, wherein at least two x-ray radiation sources have fan beams having identical fan angles.

24. A computer readable medium including program segments for, when executed on a computer device, causing the computer device to implement the method of claim 21.

25. A CT system for generating tomographic representations of an examination object containing a partial object that moves at times, comprising:
   means for scanning the examination object using a first x-ray radiation source to rotate around the examination object and to emit a first fan beam at a specific rotation angle at a first instant, and a second x-ray radiation source to rotate around the examination object and to emit a second fan beam, at the same rotation angle at a second, relatively later instant;
   means for measuring absorption of the scanning radiation upon passage through the examination object on a same radiation path at successive instants; and
   means for comparing deviating absorption values of a multiplicity of spatially equivalent and equidirectional fan beams proceeding from the same angular position of the x-ray radiation sources to deduce at least one of relative movement and relative rest of the partial object, between the first and second instants.

* * * * *